US010524524B2

(12) United States Patent
Lee

(10) Patent No.: US 10,524,524 B2
(45) Date of Patent: Jan. 7, 2020

(54) METHODS AND DEVICES FOR PROTECTIVE FILTRATION AND DELIVERY OF RESPIRABLE COMPOUNDS

(71) Applicant: James D. Lee, Armonk, NY (US)

(72) Inventor: James D. Lee, Armonk, NY (US)

(73) Assignee: F. Harlan Batrus, Mamaroneck, NY (US)

( * ) Notice: Subject to any disclaimer, the term of this patent is extended or adjusted under 35 U.S.C. 154(b) by 958 days.

(21) Appl. No.: 14/900,982

(22) PCT Filed: Jun. 27, 2014

(86) PCT No.: PCT/US2014/044726
§ 371 (c)(1),
(2) Date: Dec. 22, 2015

(87) PCT Pub. No.: WO2014/210554
PCT Pub. Date: Dec. 31, 2014

(65) Prior Publication Data

US 2017/0318874 A1 Nov. 9, 2017

Related U.S. Application Data

(60) Provisional application No. 61/840,945, filed on Jun. 28, 2013, provisional application No. 61/840,932, filed on Jun. 23, 2013, provisional application No. 61/840,915, filed on Jun. 28, 2013.

(51) Int. Cl.

| | |
|---|---|
| ***A61M 16/06*** | (2006.01) |
| ***A41D 13/11*** | (2006.01) |
| ***A62B 7/10*** | (2006.01) |
| ***A62B 23/02*** | (2006.01) |
| ***A61M 16/10*** | (2006.01) |
| *A61M 15/08* | (2006.01) |

(52) U.S. Cl.
CPC .......... *A41D 13/11* (2013.01); *A41D 13/1192* (2013.01); *A61M 16/06* (2013.01); *A61M 16/107* (2014.02); *A62B 7/10* (2013.01); *A62B 23/02* (2013.01); *A41D 2400/52* (2013.01); *A61M 15/08* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,637,383 A | | 1/1987 | Lopez et al. | |
| 5,636,628 A | * | 6/1997 | Barnum | A41D 13/1115 128/206.12 |
| 6,338,340 B1 | * | 1/2002 | Finch | A62B 18/084 128/205.27 |
| 6,872,241 B2 | * | 3/2005 | Soane | B01D 46/0001 422/120 |
| 7,004,167 B2 | * | 2/2006 | Cheng | A41D 13/1192 128/205.27 |
| 2003/0066549 A1 | * | 4/2003 | Noda | B08B 7/00 134/37 |

FOREIGN PATENT DOCUMENTS

| | | |
|---|---|---|
| WO | 2001032265 | 5/2001 |
| WO | 03039713 A1 | 5/2003 |
| WO | 2014210554 A1 | 12/2014 |

OTHER PUBLICATIONS

International Search Report for International Patent Application No. PCT/US2014/044726, dated Oct. 31, 2014 (4 pages).
Written Opinion of the International Searching Authority for International Patent Application No. PCT/US2014/044726, dated Oct. 31, 2014 (7 pages).

* cited by examiner

*Primary Examiner* — Tan-Uyen T Ho
*Assistant Examiner* — Margaret M Luarca
(74) *Attorney, Agent, or Firm* — Dorsey & Whitney LLP

(57) ABSTRACT

The present invention relates generally to methods for the delivery of beneficial respirable compounds such as moisture, anti-inflammation compounds, anti-irritants, fragrances, aromatherapy compounds, and low dose medications slowly and continuously over time using a mask containing a thickened aqueous gel media delivery system combined with, supported by, and coating solid bodies inside the filter. The present invention also relates generally to methods for the removal of harmful industrial gasses from inhaled air using a disposable filtration mask containing a fluid filter media composed of a thickened aqueous gel that can be readily modified by means of additives to enhance its filtration properties for specific gasses individually, or in combination. The fluid filter media is combined with, supported by, and coats solid bodies inside the filter which optimize contact between the fluid filtration gel and the incoming air containing harmful industrial gasses. The present invention also relates generally to methods for the removal of hydrophilic bio-particulates from inhaled air using a disposable filtration mask containing a fluid filter media composed of a thickened aqueous gel that wets the bio-particulates, increasing their effective size and mass, and then retains them using the surface tension and viscosity of the thickened aqueous gel.

15 Claims, No Drawings

METHODS AND DEVICES FOR PROTECTIVE FILTRATION AND DELIVERY OF RESPIRABLE COMPOUNDS

CROSS-REFERENCE TO RELATED APPLICATIONS

This application is a national stage application of International Application No. PCT/US2014/044726, filed Jun. 27, 2014, and entitled "METHODS AND DEVICES FOR PROTECTIVE FILTRATION AND DELIVERY OF RESPIRABLE COMPOUNDS", which claims priority to U.S. Application No. 61/840,915, filed Jun. 28, 2013, and entitled "METHOD AND DEVICES FOR PROTECTIVE FILTRATION OF BIO-PARTICULATES"; U.S. Application No. 61/840,945, filed Jun. 28, 2013, and entitled "METHOD AND DEVICES FOR PROTECTIVE FILTRATION OF BIO-PARTICULATES"; and U.S. Application No. 61/840,932, filed Jun. 28, 2013, and entitled "METHOD AND DEVICES FOR PROTECTIVE FILTRATION OF HARMFUL INDUSTRIAL GASSES", all of which are hereby incorporated by reference.

FIELD

The present disclosure relates generally to methods for protective filtration and delivery of respirable compounds.

BACKGROUND

Current filtration masks are useful to firefighters and others to aid in the delivery of oxygen and to protect from the inhalation of toxic gases and particulates in a fire fighting situation. What is needed is a filtration mask for filtration of specific gasses or bio-particulates from inhaled air that can be used and/or worn by anyone in a variety of situations, not just by fire fighting professionals in a fire fighting situation. What is also needed is a filtration mask for delivery of respirable compounds. Against this backdrop, the present disclosure was developed.

SUMMARY

The present disclosure relates generally to methods for the delivery of beneficial respirable compounds slowly and continuously over time using a mask containing an aqueous gel media delivery system combined with, supported by, and coating solid bodies inside the filter. The present disclosure also relates generally to methods for the removal of harmful industrial gasses from inhaled air using a disposable filtration mask containing a fluid filter media composed of a thickened aqueous gel that can be readily modified by means of additives to enhance its filtration properties for specific gasses individually, or in combination. The fluid filter media is combined with, supported by, and coats solid bodies inside the filter which optimize contact between the fluid filtration gel and the incoming air containing harmful industrial gasses. The present disclosure also relates generally to methods for the removal of bio-particulates from inhaled air using a disposable filtration mask containing an aqueous gel media combined with, supported by, and coating solid bodies inside the filter.

A method for delivering respirable compounds to a subject in need thereof is disclosed. The method comprising: providing a filtration mask to the subject, the mask comprising: an air permeable fabric bag having an aqueous gel filter media disposed within a chamber of the air permeable fabric bag, the filter media comprising at least one respirable compound; and placing the filtration mask over the nose and mouth of the subject; wherein the at least one respirable compound is delivered to the subject each time the subject inhales air through the filter media. The filtration mask may be disposable. The filter media may comprise beads coated with the aqueous gel filter media. The beads may be impregnated with the at least one respirable compound. The aqueous gel filter media may be modified by changing its pH. The filter media may be modified by altering a hydrophobic or hydrophilic composition of the gel and beads. The respirable compound is selected from the group consisting of water, anti-inflammatory compounds, anti-irritants, fragrances, aromatherapy compounds, and low dose medications. The respirable compound is soluble and release of the soluble respirable compound is enhanced by mixing salt capsules into the gel which can be broken, such as by squeezing, to cause the respirable compound to become less soluble and more readily aerosolized for respiration. A rate of release of the respirable compound is regulated by the total concentration of salt mixed into the gel by rupturing the salt capsules in the gel.

A method of protecting a subject from inhalation of an industrial gas is disclosed. The method comprises providing a filtration mask to the subject, the mask comprising: an air permeable fabric bag having an aqueous gel filter media disposed within a chamber of the air permeable fabric bag; and placing the filtration mask over the nose and mouth of the subject; wherein the filter media binds the industrial gas upon contact and prevents the subject from inhaling it. In some aspects, the filtration mask is disposable. In some aspects, the filter media comprises beads coated with the aqueous gel filter media. In some aspects, aqueous gel filter media is modified by changing its pH. In some aspects, wherein the filter media is modified by altering a hydrophobic or hydrophilic composition of the gel and beads. In some aspects, the pH of the filter media is increased and the industrial gas is selected from sulfuric acid, $H_2SO_4$ and nitric acid $HNO_3$. In some aspects, the pH of the filter media is increased by adding dilute sodium hydroxide, sodium carbonate, and sodium bicarbonate. In some aspects, the pH of the filter media is decreased and the industrial gas is ammonia. In some aspects, the pH of the filter media is decreased by adding dilute acetic acid. In some aspects, wherein the absorption of alkanes, alkenes, hexanes, benzenes, toluenes, and polycyclic hydrophobic compounds is enhanced by mixing small graphite flakes into the gel.

A method of protecting a subject from inhalation of one or more hydrophilic bio-particulates is disclosed. The method comprises providing a filtration mask to the subject, the mask comprising: an air permeable fabric bag having an aqueous gel filter media disposed within a chamber of the air permeable fabric bag; and placing the filtration mask over the nose and mouth of the subject; wherein the filter media binds the one or more hydrophilic bio-particulates upon contact and prevents the subject from inhaling them. In some aspects, the filtration mask is disposable.

In some aspects, the filter media comprises beads coated with the aqueous gel filter media. In some aspects, the one or more hydrophilic bio-particulates are selected from viruses, bacteria, fungi, pollen, spores and allergens.

DETAILED DESCRIPTION

The present disclosure relates generally to methods for the delivery of beneficial respirable compounds slowly and continuously over time using a mask containing an aqueous gel media delivery system combined with, supported by, and coating solid bodies inside the filter. The present disclosure also relates generally to methods for the removal of harmful industrial gasses from inhaled air using a disposable filtration mask containing a fluid filter media composed of a thickened aqueous gel that can be readily modified by means of additives to enhance its filtration properties for specific gasses individually, or in combination. The fluid filter media is combined with, supported by, and coats solid bodies inside the filter which optimize contact between the fluid filtration gel and the incoming air containing harmful industrial gasses. The present disclosure also relates generally to methods for the removal of bio-particulates from inhaled air using a disposable filtration mask containing an aqueous gel media combined with, supported by, and coating solid bodies inside the filter, and inactivation of those bio-particulates by incorporating one or more antimicrobial ingredients such as an alcohol, or peroxide into the gel.

As described herein, an aqueous gel (filter) media is contained within an air permeable tailored fabric bag that can be worn over the face, covering and protecting the nostrils and mouth of the wearer. Thickened gel, coating the exterior of the tailored fabric bag contacts the surrounding skin on the wearer's face, providing an effective seal to the skin around the filter's perimeter.

In one aspect, the disposable mask provides a low cost alternative or supplement to expensive respirators commonly used for the delivery of beneficial respirable compounds to the lungs. A disposable gel filtration mask, containing a baseline gel can be inexpensively modified to deliver the beneficial respirable compound of choice, and produced in quantity at a cost of less than a dollar. Such a mask can also deliver the beneficial respirable compound slowly and continuously over time rather than by intermittent large doses as delivered by a standard inhaler.

The baseline gel is generally aqueous and is composed of water, a plant extract such as aloe vera, and an emulsifying agent such as carbopol which also serves to thicken the gel and increase its viscosity so that it is generally retained within the filter and evenly coats the solid bodies inside the filter to ensure optimum contact between the filtered air and the gel. In all cases, all components of the gel will be materials considered to be Generally Regarded as Safe ("GRAS") by the FDA.

The properties of the baseline gel can readily be modified as needed to regulate slow, continuous delivery requirements for a given respirable compound. This can be done by shifting its pH to better deliver compounds that are either slightly acidic or slightly basic, or by modifying the amount of organic thickener in the gel and adding hydrophobic beads into the gel to enhance its delivery of hydrophilic or hydrophobic compounds.

In this manner, moisture, anti-inflammation compounds, anti-irritants, fragrances, aroma-therapy compounds, and low dose medications can be delivered to a wearer. Such masks can be used to moisturize inhaled air in arid environments, to soothe irritated lung tissues, to mask unpleasant ambient odors, to provide therapeutic compounds, or to actually deliver respirable medications on a slow, regular delivery schedule.

In one embodiment, the respirable compound can be mixed with the thickened aqueous gel. In another embodiment, the respirable compound can be impregnated into the solid beads within the gel. In another embodiment, capsules containing a salt such as sodium chloride can be mixed within the gel, and ruptured by squeezing the mask with the hands before use to release the salt into the gel, thereby causing certain miscible compounds to become less soluble, separate from the gel, and aerosolize for inhalation. In one embodiment, moisture and anti-inflammatory compounds such as aloe vera can be introduced to lungs damaged by unprotected inhalation of very hot air, by chemical irritants, or by years of smoking, or due to other exposures which might cause COPD. In another embodiment, the respirable compound may simply be an aromatherapy compound that slowly vaporizes into the inhaled airstream. In other embodiments, albuterol, steroids, corticosteroids, anesthetics, bronchodilators, or antibiotics may be delivered from the gel into the airstream. In another embodiment, ethanol, or another compound may be administered by the gel to the lungs for generally recreational purposes. In yet another embodiment, psychoactive compounds may be administered more evenly to patients over extended periods of time, with potentially better clinical outcomes.

In all cases, the gel within the filter is prevented from drying out by the wearer's own moist exhalations, allowing for extended wear and use. Similarly the carbon dioxide from the wearer's exhalations will be absorbed by filter's operating at neutral to slightly basic pHs to create an increasing buffering effect over time.

In another aspect, the present disclosure relates generally to methods for the removal of harmful industrial gasses from inhaled air using a disposable filtration mask containing a fluid filter media composed of a thickened aqueous gel that can be readily modified by means of additives to enhance its filtration properties for specific gasses individually, or in combination. The fluid filter media is combined with, supported by, and coats solid bodies inside the filter which optimize contact between the fluid filtration gel and the incoming air containing harmful industrial gasses.

The disposable filter mask provides a low cost alternative or supplement to expensive emergency respirators commonly used on industrial sites. Because such respirators are designed to handle a wide range of gasses, the cost associated with their "all threats" design is substantial, and their capabilities often greatly exceed the needs of many industrial locations where only a single hazardous gas may be in use or in production. This high cost, and the requirement to replace respirator components after each use, effectively discourages their use in all but the most life-threatening situations, whereas a low cost disposable gel filtration mask, containing a baseline gel that can be inexpensively modified to filter the specific gas in use, and produced in quantity at a cost of less than a dollar actually encourages the use of respiratory protection on a routine basis to prevent respiratory damage over time from repeated and regular low dose exposures.

The baseline gel is generally aqueous and is composed of water, a plant extract such as aloe vera, and an emulsifying agent such as carbopol which also serves to thicken the gel and increase its viscosity so that it is generally retained within the filter and evenly coats the solid bodies inside the filter to ensure optimum contact between the filtered air and the gel. In all cases, all components of the gel will be materials considered to be Generally Regarded as Safe ("GRAS") by the FDA.

The properties of the baseline gel can readily be modified as needed to enhance its filtration requirements for a given gas. To enhance its filtration for acidic gasses such as sulfuric acid, $H_2SO_4$, or nitric acid $HNO_3$, the pH of the gel can be increased to as high as 10 by adding dilute sodium hydroxide, sodium carbonate, and sodium bicarbonate. Conversely, the filtration of basic gasses, such as ammonia, NH3, can be enhanced by using a dilute acetic acid to shift the gel to a slightly acidic pH.

The properties of the baseline gel can readily be modified as needed to enhance its filtration requirements for a given gas. This can be done by shifting its pH to better absorb either acid gasses or basic gasses, by modifying the amount of organic thickener in the gel and adding hydrophobic beads into the gel to enhance its absorption of organic gasses, or by adding a compound to the gel that reacts with a specific gas to chemically convert it and capture it within the gel.

To enhance the gel's filtration for acidic gasses such as sulfuric acid, $H_2SO_4$, or nitric acid, $HNO_3$, the pH of the gel can be increased to as high as 10 by adding dilute sodium hydroxide, sodium carbonate, and sodium bicarbonate. Conversely, the filtration of basic gasses, such as ammonia, NH3, can be enhanced by using a dilute acetic acid to shift the gel to a slightly acidic pH.

To enhance the gel's filtration for organic or hydrophobic gasses, the amount of emulsifier and/or organic thickener in the gel can be increased, a carboxylate thickener with a longer hydrocarbon chain can be used as an additive, small graphite flakes, and/or hydrophobic beads can be added to the gel. The presence of some water within the gel will actually serve to drive hydrophobic gasses toward the hydrophobic beads and enhance the absorption of the hydrophobic gasses by the hydrophobic beads.

To enhance the gel's filtration of specific gasses of concern, such as hydrogen sulfide, $H_2S$, for example, a long chain alcohol can be added to the gel to cause the hydrogen sulfide to be chemically converted to a thiol and thereby trapped within the gel. Similarly, the combination of a slightly basic pH and presence of organic compounds within the filtration media, will enhance the absorption of carbon monoxide, CO, by converting it into the formate ion. Other specific gasses can be trapped as well by using the same concept of adding a compound to the gel which reacts with the gas to chemically convert the gas to a harmless compound that is retained within the gel. For example, filtration of alkanes, alkenes, benzenes, toluenes, hexanes, and polycyclic compounds can be enhanced by mixing very small graphite flakes into the gel onto which straight chain, cyclic, and polycyclic hydrophobic compounds will be driven and there adsorbed.

In all cases, the gel within the filter is prevented from drying out by the wearer's own moist exhalations, allowing for extended wear and use. Similarly the carbon dioxide from the wearer's exhalations will be absorbed by filter's operating at neutral to slightly basic pHs to create an increasing buffering effect over time.

In another aspect, the disposable filter mask provides a low cost means of protecting against viruses, bacteria, fungi, allergens, and spores. The filter can be worn for a number of applications, including, but not limited to, protection against allergens and other bio-particulates such as mold spores while working; protection against airborne microbes while riding mass transportation, to include aircraft; and to provide respiratory relief while sleeping.

The aqueous gel is composed of water, a plant extract such as aloe vera, and an emulsifying agent such as carbopol which also serves to thicken the gel and increase its viscosity so that it is generally retained within the filter and evenly coats the solid bodies inside the filter to ensure optimum contact between the filtered air and the gel. In all cases, all components of the gel will be materials considered to be Generally Regarded as Safe ("GRAS") by the FDA.

The aqueous gel filter is not dependent upon using a small pore size for filtration of small bio-particulates as is common with all other filter media. Instead, the aqueous gel bio-particulate filter operates by effectively increasing the size and mass of the bio-particulate to be filtered.

Upon encountering the thickened aqueous gel, hydrophilic bio-particulates become wetted, both absorbing moisture and becoming coated by the thickened gel itself. This effectively increases the size and mass of the bio-particulate, allowing it to easily be retained by the thickened gel due to both the surface tension of the gel and its viscosity.

In such a manner hydrophilic bio-particulates as small as viruses, approximately 0.3 microns, can be filtered by the gel, preventing their inhalation, and providing filtration as effective as that of a HEPA filter.

Further, the gel within the filter is prevented from drying out by the wearer's own moist exhalations, allowing for extended wear and use for intervals as long as eight hours, permitting it to be used throughout a night's sleep, over the course of a workday, or for the duration of an international flight. Similarly the carbon dioxide from the wearer's exhalations will be absorbed by filter's operating at neutral to slightly basic pHs to create an increasing buffering effect over time.

What is claimed is:

1. A method for delivering respirable compounds to a subject in need thereof, comprising:

providing a filtration mask to the subject, the mask comprising: an air permeable fabric bag having an aqueous gel filter media disposed within a chamber of the air permeable fabric bag, the aqueous gel filter media comprising at least one respirable compound; and placing the filtration mask over the nose and mouth of the subject, wherein the at least one respirable compound is delivered to the subject each time the subject inhales air through the aqueous gel filter media, and wherein the respirable compound is soluble and release of the soluble respirable compound is enhanced by mixing salt capsules into the gel, the salt capsules configured to be broken before use of the filtration mask to cause the respirable compound to become less soluble and more readily aerosolized for respiration.

2. The method of claim 1, wherein the filtration mask is disposable.

3. The method of claim 1, wherein the aqueous gel filter media comprises beads coated with the aqueous gel filter media.

4. The method of claim 3, wherein the beads are impregnated with the at least one respirable compound.

5. The method of claim 3, wherein the aqueous gel filter media is modified by altering a hydrophobic or hydrophilic composition of the gel and beads.

6. The method of claim 1, wherein the aqueous gel filter media is modified by changing its pH.

7. The method of claim 1, wherein the respirable compound is selected from the group consisting of water, anti-inflammatory compounds, anti-irritants, fragrances, aromatherapy compounds, and low dose medications.

8. The method of claim 1, wherein a rate of release of the respirable compound is regulated by the total concentration of salt mixed into the gel by rupturing the salt capsules in the gel.

9. A method for delivering respirable compounds to a subject in need thereof, comprising:

providing a filtration mask to the subject, the mask comprising: an air permeable fabric bag having an aqueous gel filter media disposed within a chamber of the air permeable fabric bag, the aqueous gel filter media comprising at least one respirable compound; and placing the filtration mask over the nose and mouth of the subject;

wherein:

the at least one respirable compound is delivered to the subject each time the subject inhales air through the aqueous gel filter media;

the respirable compound is soluble and release of the soluble respirable compound is enhanced by mixing salt capsules into the gel, the salt capsules configured to be broken before use of the filtration mask to cause the respirable compound to become less soluble and more readily aerosolized for respiration, and a rate of release of the respirable compound is regulated by the total concentration of salt mixed into the gel by rupturing the salt capsules in the gel.

10. The method of claim 9, wherein the filtration mask is disposable.

11. The method of claim 9, wherein the aqueous gel filter media comprises beads coated with the aqueous gel filter media.

12. The method of claim 11, wherein the beads are impregnated with the at least one respirable compound.

13. The method of claim 11, wherein the aqueous gel filter media is modified by altering a hydrophobic or hydrophilic composition of the gel and beads.

14. The method of claim 9, wherein the aqueous gel filter media is modified by changing its pH.

15. The method of claim 9, wherein the respirable compound is selected from the group consisting of water, anti-inflammatory compounds, anti-irritants, fragrances, aromatherapy compounds, and low dose medications.

* * * * *